(12) United States Patent
Tulley

(10) Patent No.: US 10,426,077 B2
(45) Date of Patent: Oct. 1, 2019

(54) SEED FLOW LUBRICANT COMPOSITIONS AND USES THEREOF

(71) Applicant: 3 Star Ag LLC, Calamus, IA (US)

(72) Inventor: Brian Tulley, Calamus, IA (US)

(73) Assignee: 3 Star Ag LLC, Calamus, IA (US)

( * ) Notice: Subject to any disclaimer, the term of this patent is extended or adjusted under 35 U.S.C. 154(b) by 0 days.

(21) Appl. No.: 15/872,339

(22) Filed: Jan. 16, 2018

(65) Prior Publication Data

US 2018/0228077 A1     Aug. 16, 2018

Related U.S. Application Data

(60) Provisional application No. 62/458,779, filed on Feb. 14, 2017.

(51) Int. Cl.

| | |
|---|---|
| *A01N 25/00* | (2006.01) |
| *A01N 25/08* | (2006.01) |
| *A01C 1/06* | (2006.01) |
| *C09K 3/22* | (2006.01) |
| *A01C 15/00* | (2006.01) |

(52) U.S. Cl.
CPC ................ *A01C 1/06* (2013.01); *A01N 25/00* (2013.01); *A01N 25/08* (2013.01); *C09K 3/22* (2013.01); *A01C 15/003* (2013.01)

(58) Field of Classification Search
None
See application file for complete search history.

(56) References Cited

U.S. PATENT DOCUMENTS

| | | | |
|---|---|---|---|
| 4,608,203 A * | 8/1986 | Akasaka | .................. A23J 3/16 |
| | | | 530/378 |
| 2002/0032233 A1* | 3/2002 | Saebo | ..................... C11B 3/001 |
| | | | 514/549 |

| | | | |
|---|---|---|---|
| 2012/0135125 A1 | 5/2012 | Muschiolik | |
| 2012/0220454 A1 | 8/2012 | Chen | |
| 2015/0072857 A1 | 3/2015 | Reichert et al. | |
| 2016/0007590 A1 | 1/2016 | Schultz | |

FOREIGN PATENT DOCUMENTS

| | | | |
|---|---|---|---|
| CA | 2861526 | | 10/2013 |
| CN | 104705230 A | * | 6/2015 |
| WO | 2013/150261 | | 10/2013 |
| WO | 2018/151884 | | 8/2018 |

OTHER PUBLICATIONS

Costa et al.(Use of ultrafiltration and supercritical fluid extraction to obtain a whey buttermilk powder enriched in milk fat globule membrane phospholipids, International dairy journal (2010), vol. 20, No. 9, pp. 598-602) (Year: 2010).*
Su et al.(The nutritional value of fish protein concentrate, Nutrition reports international (1982), vol. 25, No. 3, pp. 567-572, charts) (Year: 1982).*
Sathivel et al.( Physical and nutritional properties of catfish roe spray dried protein powder and its application in an emulsion system, Journal of Food Engineering (2009), vol. 95, No. 1, pp. 76-81) (Year: 2009).*
Niki et al.( The process of producing active fish protein powder, Bulletin of the Japanese Society of Scientific Fisheries. vol. 48, No. 7, pp. 999-1004. (Year: 1982).*
Assis et al. "Protein hydrophobic dressing on seeds aiming at the delay of undesirable germination," Sci. Agric. (Piracicaba, Braz.), 2009, 66(1):123-126.
International Search Report and Written Opinion dated May 15, 2018 from related international application No. PCT/US2018/013805, 8 pp.

\* cited by examiner

*Primary Examiner* — Alton N Pryor
(74) *Attorney, Agent, or Firm* — Polsinelli PC

(57) ABSTRACT

Dry compositions comprising protein powders and lipids for use as seed flow lubricants, and methods of using the dry composition to improve seed flowability, reduce formation of seed dust, increase seed plantability, increase plant emergence, and increase crop yield.

21 Claims, 4 Drawing Sheets

SEED FLOW LUBRICANT COMPOSITIONS AND USES THEREOF

CROSS-REFERENCE TO RELATED APPLICATIONS

This application claims the priority of U.S. Provisional Application Ser. No. 62/458,779, filed Feb. 14, 2017, the disclosure of which is hereby incorporated by reference in its entirety.

FIELD

The present disclosure relates to dry compositions for use as seed flow lubricants, wherein the dry compositions comprise protein powders and lipids. As such, the dry compositions are non-toxic and biodegradable.

BACKGROUND

Seed flow lubricants are materials that are added to the planter box to improve seed flow in the planter. Such lubricants generally are added when the seed is loaded into the planter box, or they may be metered in during planting. Since seed flow lubricants are generally powders, significant airborne lubricant dust can arise during planting. Commonly used seed flow lubricants include talc and graphite, both of which can cause nose, throat, eye, and skin irritation. Further, when graphite and talc are used as seed flow lubricants, they tend to abrade the surfaces of the seeds creating seed dust. Dust from untreated seeds primarily consists of naturally occurring components of the seed such as chaff and the seed hull, and dust from treated seeds further comprises components of the seed treatment (e.g., fungicide, insecticide, and the like). The seed dust can become airborne and cause problems to humans, animals, and insects. Thus, there is a need for biodegradable, environmentally friendly, and less toxic seed flow lubricants.

SUMMARY

Among the various aspects of the present disclose are dry compositions comprising protein powders and lipids for use as seed flow lubricants.

Another aspect of the present disclosure provides methods for improving plant seed flowability and/or reducing formation of plant seed dust, wherein the methods comprise contacting a plurality of plant seeds with a dry composition comprising a protein powder and a lipid.

A further aspect of the present disclosure encompasses a seed composition comprising a plurality of plant seeds and a dry composition comprising a protein powder and a lipid.

Other aspects and iterations of the disclosure are detailed below.

DETAILED DESCRIPTION

Figure 1:
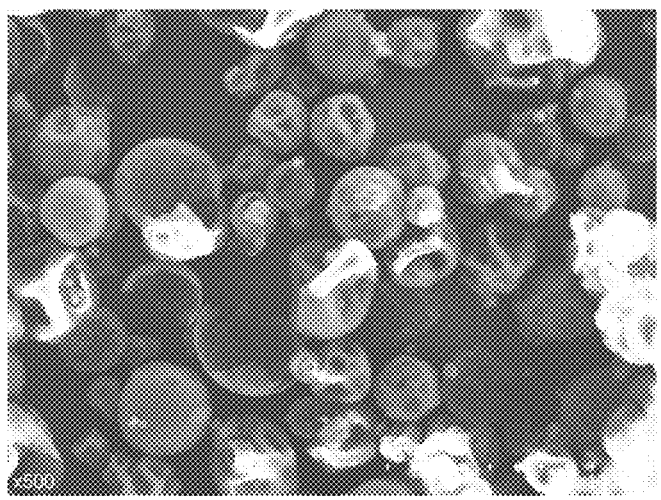
FIG. 1 presents a micrograph of the soy-based seed lubricant disclosed herein.

The present disclosure provides dry compositions comprising protein powders and lipids for use as seed flow lubricants. The dry compositions reduce seed-to-seed friction, thereby increasing seed flowability, seed plantability, and planting uniformity. Additionally, dry compositions comprising protein powders are less abrasive to seed coatings than the standard platy lubricants, resulting in the formation of less seed dust. Advantageously, the dry seed lubricant compositions disclosed herein are non-toxic, biodegradable, and environmentally friendly. Additionally, the nitrogen provided by the protein powder in the dry composition may be beneficial to plant growth and crop yield.

(I) Seed Flow Lubricant Compositions

One aspect of the present disclosure provides dry compositions for use as seed flow lubricants. The dry compositions comprise at least one protein powder and at least one lipid. In some embodiments, the dry compositions may further comprise at least one additional agent. For example, the dry composition may further comprise at least one active ingredient and/or at least one inert ingredient.

(a) Protein Powders

The dry compositions disclosed herein comprise at least one protein powder. A variety of protein powders are suitable for use in the dry composition. In general, the protein powder may be or may be obtained from a plant protein powder, an animal protein powder, a fungal protein powder, a bacterial protein powder, or a combination thereof.

In some embodiments, the protein may be a plant protein. Non-limiting examples of suitable plant proteins include soy protein, corn protein, oat protein, wheat protein, pea protein, rice protein, nut protein, algal (e.g., Spirulina) protein, or kelp protein. In other embodiments, the protein may be an animal protein. Examples of suitable animal proteins include, without limit, whey protein, casein protein, egg protein, albumen protein, blood meal protein, bone meal protein, fish protein, shellfish protein, or plankton protein. In yet other embodiments, the protein may be a fungal protein chosen from brewer's yeast protein (i.e., *Saccharomyces cerevisiae*) or a probiotic yeast protein (e.g., *Saccharomyces cerevisiae, Saccharomyces boulardii*, or *Kluyveromyces lactis*). In additional embodiments, the protein may be a bacterial protein. For example, the bacterial protein may be derived from probiotic bacteria such as *Lactobacillus, Bifidobacterium*, or *Bacillus*.

In specific embodiments, the protein powder may be a soy protein powder. In some embodiments, the soy protein powder may be an isolated soy protein powder. In certain embodiments, the isolated soy protein powder may be a soy protein concentrate. In other embodiments, the isolated soy protein powder may be a soy protein isolate. Soy protein powders comprise soy protein polymers. Among the fundamental characteristics of soy protein polymers are large hydrated volume, high glass transition temperature, amphoteric behavior (net charge of molecule depends on pH of the environment in which it exists) and amphiphilic behavior (possesses both hydrophilic and hydrophobic regions).

Soy protein concentrates are made by repeatedly washing defatted soybean flakes with water, which may optionally contain low levels of food grade alcohols or buffers. The effluent from the repeated washings is discarded, and the solid residue is dried, producing the desired soy protein concentrate. Soy protein isolates are typically made by extracting defatted soy flakes or soy flour under alkaline conditions (pH 7-12). The extract is adjusted to pH 4.5 with acids such as sulfuric, hydrochloric, phosphoric or acetic acid. At a pH of 4.5 (the approximate isoelectric point), soy proteins precipitate and may readily be separated mechanically. The protein precipitate may be processed thermally, chemically, and/or enzymatically (e.g., the isolated soy protein may be hydrolyzed), and the isolate is dried. For example, the isolated soy protein precipitate may be spray dried to produce an isolated soy protein powder comprising spherically shaped particles (see FIG. 1).

The pH of both soy protein concentrates or soy protein isolates may be adjusted to reach a target value prior drying to produce the final product. Soy protein isolates contain essentially no carbohydrate or lipid. The soy protein concentrate or soy protein isolate may further comprise from about 6% to about 15% of ash on a dry weight basis. The pH of the soy protein powder may range from 6 to 10. In further embodiments, the soy protein powder may have a high viscosity range at 12% solids of between about 70 and about 150 milli Pascal-second (mPas-s). In other embodiments, the soy protein powder may have a low viscosity range at 14% solids of between 30 and about 150 mPas-s.

The amount of protein powder present in the dry composition can and will vary depending upon the type of protein powder and/or the presence and identity of additional agents. In general, the dry composition may comprise from about 50% to about 99.9% of the protein powder by weight of the dry composition. In various embodiments, the dry composition may comprise at least 60%, at least 70%, at least 80%, at least 90%, at least 95%, or at least 99% of the protein powder by weight of the dry composition. In embodiments in which the protein powder is a soy protein powder, the dry composition may comprise at least about 80%, at least about 85%, at least about 90%, or at least about 95% of soy protein powder by weight of the dry composition. In embodiments in which the protein is soy protein isolate, the amount of soy protein may be at least 90%, at least 92%, at least 94%, at least 96%, at least 97%, at least 98%, or at least 99% by weight of the dry composition.

(b) Lipids

The dry compositions disclosed herein further comprise at least one lipid. In some embodiments, the lipid may be a phospholipid such as a lecithin. The lecithin may be derived from soy, sunflower, corn, peanuts, grains, or eggs. In other embodiments, the lipid may be an oil or a fat. Suitable oils include vegetable oils, such as, for example, include soy oil, coconut oil, corn oil, cottonseed oil, palm oil, peanut oil, rapeseed oil, safflower oil, or sunflower oil, or fish oils, such as, for example, anchovy oil, herring oil, krill oil, mackerel oil, salmon oil, or sardine oil. Suitable fats include animals fats such as beef tallow, pork fat, lamb fat, chicken fat, butter fat, and the like.

In specific embodiments, the lipid may be soy lecithin.

The amount of lipid in the dry composition can and will vary depending, for example, on the type of protein powder in the dry composition. In general, the dry composition may comprise from about 0.005% to about 5% of the lipid by weight of the dry composition. In various embodiments, the amount of lipid may range from about 0.005% to about 0.05%, from about 0.05% to about 0.5%, from about 0.5% to about 1%, or from about 1% to about 5% by weight of the dry composition. In embodiments in which the lipid is soy lecithin, the dry composition may comprise from about 0.01% to about 5% of soy lecithin by weight of the dry composition.

(c) Active Ingredients

In certain embodiments, the dry composition may further comprise at least one active ingredient. Suitable active ingredients include micronutrients, *rhizobium* inoculums, fertilizers, insecticides, fungicides, herbicides, or combinations thereof.

In some embodiments, the at least one active ingredient may be a micronutrient. Soil micronutrients include boron, chlorine, copper, iron, manganese, molybdenum, and zinc. In some embodiments, the micronutrient may be cobalt, silicon, or vanadium.

In other embodiments, the at least one active ingredient may be a *rhizobium* inoculum. Non-limiting examples of agriculturally relevant *rhizobia* include *Rhizobium leguminosarum, Rhizobium loti, Rhizobium meliloti, Rhizobium trifolii, Bradyrhizobium japonicum*, and *Mesorhizobium ciceri*.

In further embodiments, the at least one active ingredient may be a fertilizer. Suitable fertilizers include, without limit, nitrogen (N) fertilizers, phosphate (P) fertilizers, potassium (K) fertilizers, NP fertilizers, NK fertilizers, PK fertilizers, and NPK fertilizers. In certain embodiments, the fertilizer may contain one or more secondary macronutrients such as calcium, magnesium, and/or sulfur. In other embodiments, the fertilizer may also contain one or more micronutrients. In further embodiments, the fertilizer may be synthetic or commercial. In other embodiments, the fertilizer may be organic and contain plant and/or animal derived organic matter. In general, the fertilizer is in a solid form. In certain embodiments, the fertilizer may provide slow or controlled release of the nutrients.

In additional embodiments, the at least one active ingredient may be an insecticide. In some embodiments, the insecticide may be a neonicotinoid. Non-limiting examples of suitable neonicotinoids include abamectin, acetamiprid, clothianidin, dinotefuran, imidacloprid, nitenpyram, nithiazine, thiacloprid, and thiamethoxam. In other embodiments, the insecticide may be an organophosphate. Suitable organophosphates include O,O-diethyl O-(2-isopropyl-4-methyl-6-pyrimidinyl)phosphorothioate, O,O-dimethyl S-2-[(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl) phosphorodithioate, O,O-dimethyl S-2-[(ethylthio)ethyl]phosphorodithioate, O,O-diethyl S-2-[(ethylthio)ethyl] phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl O-(3-methyl-4-methylmercaptophenyl)thiophosphate, O-ethyl O-p-cyanophenyl phenylphosphorothioate, O,O-dimethyl-S-(1,2-dicarboethoxyethyl) phosphorodithioate, 2-chloro-(2,4,5-trichlorophenyl) vinyldimethyl phosphate, 2-chloro-1-(2,4-dichlorophenyl) vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl] O,O-diethyl phosphorodithioate, 2-chloro-1-(2,4-dichlorophenyl)vinyl diethylphosphate, O,O-diethyl O-(3-oxo-2-phenyl-2H-pyridazine-6-yl) phosphorothioate, O,O-dimethyl S-(1-methyl-2-ethylsulfinyl)-ethyl phosphorothiolate, O,O-dimethyl S-phthalimidomethyl phosphorodithioate, O,O-diethyl S-(N-ethoxycarbonyl-N-methylcarbamoylmethyl)phosphorodithioate, O,O-dimethyl S-[2-methoxy-1,3,4-thiadiazol-5-(4H)-onyl-(4)-methyl] dithiophosphate, 2-methoxy-4H-1,3, 2-benzooxaphosphorine 2-sulfide, O,O-diethyl O-(3,5,6-trichloro-2-pyridyl)phosphorothiate, O-ethyl O-2,4-dichlorophenyl thionobenzene phosphonate, S-[4,6-diamino-s-triazine-2-yl-methyl] O,O-dimethyl phosphorodithioate, O-ethyl O-p-nitrophenyl phenyl phosphorothioate, O,S-dimethyl N-acetyl phosphoroamidothioate, 2-diethylamino-6-methylpyrimidine-4-yl-diethylphosphorothionate, 2-diethylamino-6-methylpyrimidine-4-yl-dimethylphosphorothionate, O,O-diethyl O-N-(methylsulfinyl) phenyl phosphorothioate, O-ethyl S-propyl O-2,4-dichlorophenyl phosphorodithioate, and cis-3-(dimethoxyphosphinoxy)N-methyl-cis-crotone amide. In additional embodiments, the insecticide may be a carbamate. Non-limiting examples of suitable carbamates include 1-naphthyl N-methylcarbamate, S-methyl N-[methylcarbamoyloxy]thioacetoimidate, m-tolyl methylcarbamate, 3,4-xylyl methylcarbamate, 3,5-xylyl methylcarbamate, 2-sec-butylphenyl N-methylcarbamate, 2,3-dihydro-2,2-dimethyl-7-benzofuranylmethylcarbamate, 2-isopropoxyphenyl N-methylcarbamate, 1,3-bis(carbamoylthio)-2-(N,N-dimethylamino)propane hydrochloride, and 2-diethylamino-6-methylpyrimidine-4-yl-dimethylcarbamate. In still other embodiments, the insecticide may be chosen from N,N-dimethyl N'-(2-methyl-4-chlorophenyl)formamidine hydrochloride, nicotine sulfate, milbemycin, 6-methyl-2,3-quinoxalinedithiocyclic S,S-dithiocarbonate, 2,4-dinitro-6-sec-butylphenyl dimethylacrylate, 1,1-bis(p-chlorophenyl) 2,2,2-trichloroethanol, 2-(p-tert-butylphenoxy)isopropyl-2'-chloroethylsulfite, azoxybenzene, di-(p-chlorophenyl)-cyclopropyl carbinol, di[tri(2,2-dimethyl-2-phenylethyl)tin] oxide, 1-(4-chlorophenyl)-3-(2,6-difluorobenzoyl) urea, and S-tricyclohexyltin O,O-diisopropylphosphorodithioate.

In other embodiments, the at least one active ingredient may be a fungicide. Suitable fungicides include, without limit, carbamate fungicides such as 3,3'-ethylenebis(tetrahydro-4,6-dimethyl-2H-1,3,5-thiadiazine-2-thione), zinc or manganese ethylenebis(dithiocarbamate), bis(dimethyldithiocarbamoyl)disulfide, zinc propylenebis(dithiocarbamate, bis(dimethyldithiocarbamoyl)ethylenediamine, nickel dimethyldithiocarbamate, methyl 1-(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate, and 5-methyl-10-butoxycarbonylamino-10,11-dehydrodibenzo (b,f)azepine; pyridine fungicides such as zinc bis(1-hydroxy-2(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6-diethylphenyl) phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1,4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-s-triazol(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1-2,4-thiadiazole; 2,4-dichloro-6-(O-chloroanilino)-1,3,5-triazine; 2,3-dicyano-1,4-dithioanthraquinone; copper 8-quinolinate, polyoxine; validamycin; cycloheximide; iron methanearsonate; diisopropyl-1,3-dithiolane-2-iridene malonate; 3-allyloxy-1,2-benzoisothiazol-1,1-dioxide; kasugamycin; blasticidin S; 4,5,6,7-tetrachlorophthalide; 3-(3,5-dichlorophenyl)-5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(2'-methoxyacetyl)alaninate; N-propyl-N-[2-(2,4,6-trichlorophenoxy)ethyl]imidazol-1-carboxamide; N-(3,5-dichlorophenyl)succinimide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolo[3,2,1-i,j]quinoline-2-one; 3'-isopropoxy-2-methylbenzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenylsulfamide; ethyl-N-(3-dimethylaminopropyl)thiocarbamate hydrochloride; piomycin; S,S-6-methylquinoxaline-2,3-diyldithiocarbonate; complex of zinc and manneb; di-zinc bis(dimethyldithiocarbamate) ethylenebis (dithiocarbamate) and glyphosate; chlorothalonil-based fungicides, strobilurin-based fungicides such as azoxystrobin, pyraclostrobin, and trifloxystrobin; and triazole-based fungicide such as myclobutanil, propiconazole, tebuconazol, and tetraconazole.

In yet other embodiments, the at least one active ingredient may be a herbicide. Non-limiting examples of suitable herbicides include imidazolinone, acetochlor, acifluorfen, aclonifen, acrolein, AKH-7088, alachlor, alloxydim, ametryn, amidosulfuron, amitrole, ammonium sulfamate, anilofos, asulam, atrazine, azafenidin, azimsulfuron, BAS 620H, BAS 654 00H, BAY FOE 5043, benazolin, benfluralin, benfuresate, bensulfuron-methyl, bensulide, bentazone, benzofenap, bifenox, bilanafos, bispyribac-sodium, bromacil, bromobutide, bromofenoxim, bromoxynil, butachlor, butamifos, butralin, butroxydim, butylate, cafenstrole, carbetamide, carfentrazone-ethyl, chlormethoxyfen, chloramben, chlorbromuron, chloridazon, chlorimuron-ethyl, chloroacetic acid, chlorotoluron, chlorpropham, chlorsulfuron, chlorthal-dimethyl, chlorthiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-dichlorophenoxyacetic acid, daimuron, dalapon, dazomet, 4-(2,4-dichlorophenoxy)butanoic acid, desmedipham, desmetryn, dicamba, dichlobenil, dichlorprop, dichlorprop-P, diclofop-methyl, difenzoquat metilsulfate, diflufenican, dimefuron, dimepiperate, dimethachlor, dimethametryn, dimethenamid, dimethipin, dimethylarsinic acid, dinitramine, dinocap, dinoterb, diphenamid, diquat dibromide, dithiopyr, diuron, DNOC, EPTC, esprocarb, ethalfluralin, ethametsulfuron-methyl, ethofumesate, ethoxysulfuron, etobenzanid, fenoxaprop-P-ethyl, fenuron, ferrous sulfate, flamprop-M, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupropanate, flupyrsulfuron-methyl-sodium, flurenol, fluridone, flurochloridone, fluroxypyr, flurtamone, fluthiacet-methyl, fomesafen, fosamine, glufosinate-ammonium, glyphosate, glyphosinate, halosulfuron-methyl, haloxyfop, HC-252, hexazinone, imazamethabenz-methyl, imazamox, imazapyr, imazaquin, imazethapyr, imazosuluron, imazilinone, indanofan, ioxynil, isoproturon, isouron, isoxaben, isoxaflutole, lactofen, lenacil, linuron, MCPA, MCPA-thioethyl, MCPB, mecoprop, mecoprop-P, mefenacet, metamitron, metazachlor, methabenzthiazuron, methylarsonic acid, methyldymron, methyl isothiocyanate, metobenzuron, metobromuron, metolachlor, metosulam, metoxuron, metribuzin, metsulfuron-methyl, molinate, monolinuron, naproanilide, napropamide, naptalam, neburon, nicosulfuron, nonanoic acid, norflurazon, oleic acid (fatty acids), orbencarb, oryzalin, oxadiargyl, oxadiazon, oxasulfuron, oxyfluorfen, paraquat dichloride, pebulate, pendimethalin, pentachlorophenol, pentanochlor, pentoxazone, petroleum oils, phenmedipham, picloram, piperophos, pretilachlor, primisulfuron-methyl, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, pyrithiobac-sodium, quinclorac, quinmerac, quinoclamine, quizalofop, quizalofop-P, rimsulfuron, sethoxydim, siduron, simazine, simetryn, sodium chlorate, STS system (sulfonylurea), sulcotrione, sulfentrazone, sulfometuron-methyl, sulfosulfuron, sulfuric acid, tar oils, 2,3,6-TBA, TCA-sodium, tebutam, tebuthiuron, terbacil, terbumeton, terbuthylazine, terbutryn, thenylchlor, thiazopyr, thifensulfuron-methyl, thiobencarb, tiocarbazil, tralkoxydim, tri-allate, triasulfuron, triaziflam, tribenuron-methyl, triclopyr, trietazine, trifluralin, triflusulfuron-methyl, and vernolate.

The amount of micronutrient, *rhizobium* inoculum, fertilizer, insecticide, fungicide, and/or herbicide included in the dry composition can and will vary depending upon the identity of the active ingredient. Suitable amounts or concentrations of each are well known in the art.

(d) Inert Ingredients

In other embodiments, the dry composition may further comprise at least one inert ingredient. Non-limiting examples of suitable inert ingredients include silicon dioxide, starches, starch glycolates, bentonite, diatomaceous earth, kaolin, celluloses, microcrystalline cellulose, stearates (e.g., magnesium or calcium stearate), colorants or dyes.

The amount of inert ingredient present in the dry composition may be less that about 50%, less than about 40%, less than about 30%, less than about 20%, less than about 10%, less than about 5%, less than about 2.5%, less than about 1%, less than about 0.3%, less than about 0.1%, or less than about 0.03% by weight of the dry composition.

(e) Exemplary Seed Flow Lubricant Compositions

In general, the dry compositions comprise isolated soy protein powders. The isolated soy protein powder may be soy protein concentrate or soy protein isolate. The soy protein isolate may be a hydrolyzed soy protein isolate. In some embodiments, the dry composition comprises a soy protein isolate and a soy lecithin. In other embodiments, the dry composition consists essentially of a soy protein isolate and a soy lecithin. In still other embodiments, the dry composition consists of a soy protein isolate and a soy lecithin. In certain embodiments, the dry composition comprises at least 95%, at least 96%, at least 97%, at least 98%, or at least 99% of the soy protein isolate and less than 5%, less than 4%, less than 3%, less than 2%, or less than 1% of the soy lecithin by weight of the dry composition.

The dry compositions disclosed herein are devoid of talc, graphite powder, and synthetic polymers.

(II) Seed Compositions

Another aspect of the present disclosure provides a seed composition comprising a plurality of plant seeds and any of the dry compositions detailed above in section (I).

In some embodiments, the plant seeds may be corn or maize seeds. Corn or maize seeds refers to any seed from a *Zea mays* plant that is used for food-related production or other industrial purpose such as starch production, bio-fuel manufacture (e.g., ethanol manufacture), animal fodder production and the like. Examples of *Zea mays* varieties used in industry include flour corn (*Zea mays* var. *Amylacea*), popcorn used as a food and in packaging materials (*Zea mays* var. *Evert*), flint corn used for hominy production (*Zea mays* var. *Indurata*), sweet corn used as a food (*Zea mays* var. *saccharata* and *Zea mays* var. *Rugosa*), waxy corn used in producing food thickening agents, in the preparation of certain frozen foods, and in the adhesive industry (*Zea mays* var. *Ceratina*), Amylomaize used in the production of biodegradeable plastics (*Zea mays*), striped maize used as an ornamental (*Zea mays* var. *Japonica*), blue corn (*Zea mays* var. *amylacea*), silver queen corn, golden bantam, early sunglow, Indian corn, sugar corn, pole corn, field corn, dent corn, flint corn, and flour corn.

In other embodiments, the plant seeds may be legume plant seeds or the seeds of leguminous plants. Examples of legume plant seeds include seeds of legume species of the family Fabaceae that includes species such as alfalfa (*Medicago sativa*), Austrian winter pea (*Pisum sativum*), berseem clover (*Trifolium alexandrinum*), black medic (*Medicago lupulina*), chickling vetch/pea (*Lathyrus sativus*), cowpea (*Vigna unguiculata*), crimson clover (*Trifolium incamatum*), field peas (*Pisum sativum* subsp. *arvense*), hairy vetch (*Vicia villosa*), horse beans (*Vicia faba*), kura clover (*Trifolium ambiguum*), mung bean (*Vigna radiate*), red clover (*Trifolium pratense*), soy beans (*Glycine max*), subterranean clover (*Trifolium subterraneum*), sunn hemp (*Crotalaria juncea L*), white clover (*Trifolium repens*), white sweet clover (*Melilotus alba*), woolypod vetch (*Vicia villosa* ssp. *dasycarpa*), yellow sweet clover (*Melilotus officinalis*), adzuki bean, (*Vigna angularis*, syn.: *Phaseolus angularis*), broad bean (*V. faba* var. major), field bean (*Vicia faba*), vetch (*Vicia sativa*), common beans (*Phaseolus vulgaris*), including green beans, runner beans, haricot beans and the like, chick pea (*Cicer arietinum*), guar bean (*Cyamopsis tetragonoloba*), hyacinth bean (*Dolichos lablab*), lentil (*Lens culinaris*), lima bean (*Phase lus lunatus*), lupin (*Lupinus* spp.), pea (*Pisum sativum*), peanut (*Arachis hypogaea*), pigeon pea (*Cajanus cajan*), and tepary bean (*Phaseolus acutifolius*).

In yet other embodiments, the plant seeds may be cereal seeds. Cereal seeds include invention include seeds of rice (*Owe sativa*), wheat (*Triticum* spp. such as *T. aestivum*) including species such as spelt (*T. spelta*), einkorn (*T. monococcum*), emmer (*T. dicoccum*) and durum (*T. durum*), barley (*Hordeum vulgare*) including two row and six row barley, sorghum (*Sorghum bicolor*), millet species such as pearl millet (*Pennisetum glaucum*), foxtail millet (*Setaria italica*), proso millet (*Panicum miliaceum*) and finger millet (*Eleusine coracana*), oats (*Avena sativa*), rye (*Secale cereale*), triticale (*x Triticosecale*), and buckwheat (*Fagopyrum esculentum*).

In still other embodiments, the plants seeds may be grass seeds for lawns, pastures, forage uses, cover crops, and turf uses. Suitable grass seeds include ryegrass (e.g., annual ryegrass, perennial ryegrass, winter ryegrass, Italian ryegrass, hybrid ryegrass), bluegrass (e.g., Kentucky), and fescue (e.g., red fescue, fescue, meadow fescue, tall fescue, Lucerne fescue).

In further embodiments, the plant seeds may be cotton seeds (*Gossypium hirsutum*), oil seeds of the Crucifer family, such as canola (*B. campestris*) and oilseed rape (*B. napus*), seeds of other Crucifer plant species including those of plants of the *B. oleraceae* such as seeds of cabbages, broccolis, cauliflowers, kales, Brussels sprouts, and kohlrabis; seeds of alliums including onion, leek and garlic. Other suitable field crop plant seeds include capsicums, tomatoes, cucurbits such as cucumbers, cantaloupes, summer squashes, pumpkins, butternut squashes, tropical pumpkins, calabazas, winter squashes, watermelons, lettuces, zucchinis, eggplants, beets, carrots, parsnips, rutabaga, turnips, sugar beets, celeriacs, Jerusalem artichokes, artichokes, bok choi, celery, Chinese cabbage, horse radish, musk melons, parsley, radish, spinach, linseed, sunflower, safflower, sesame, carob, coriander, mustard, grape, flax, dika, hemp, okra, poppy, castor, jojoba, and the like.

In some embodiments, the plant seeds may be untreated seeds, i.e., seeds that have not been treated using any chemical, biological, or physical method. In other embodiments the plant seeds may be treated plant seeds, i.e., seeds that have been treated or coated with one or more active ingredients. Suitable active ingredients include fertilizers, plant growth regulators, fungicides, insecticides, or combinations thereof. The seed treatment or coating may further comprise synthetic polymers in combination with the active ingredient(s). Examples of polymers used to coat plant seeds include petroleum-based polymers such as polyvinyl alcohol (also known as PVOH), polyacrylic acids, polymethacrylic acids, polyacrylates, polymethacrylates, polyvinyls, polyvinyl acetates, polyurethanes, polyurethane acrylics, polyesters, polyethylene oxides, polypropylene oxides, cellulose derived polymers such as methyl cellulose, ethyl cellulose, hydroxypropylmethyl cellulose, hydroxypropyl cellulose, or hydroxypropylethyl cellulose, combinations thereof, or co-polymers of any of the foregoing.

The amount of dry composition present in the seed composition can and will vary depending upon the components in the dry composition and the type of seeds. In general, the amount of dry composition present in the seed composition may range from about 0.0001% to about 0.5% by weight of the seed composition. In some embodiments, the amount of dry composition present in the seed composition may range from about 0.005% to about 0.01% by weight of the seed composition (e.g., about 4-8 ounces per 50 pounds of seed).

(III) Methods

Also provided herein are methods of using the dry compositions disclosed herein as seed flow lubricants to improve plant seed flowability, reduce seed-to-seed friction, reduce formation of plant seed dust, increase seed plantability, improve uniformity of planting, increase plant emergence, and increase crop yield. The methods comprise contacting a plurality of plant seeds with any of the dry compositions detailed above in section (I). Suitable plant seeds are described above in section (II).

In some embodiments, the contacting step may occur in a seed planter (e.g., in the seed planter box or hopper). For example, the seeds may be added to the seed planter box and then the dry composition may be added to the seeds in the seed planter box. The dry composition may be actively mixed with the seeds, or the dry composition may be allowed to passively mix with the seeds by gravity and movement of the seeds through the box. In other aspects, the dry composition may be added to the seed planter box and then the seeds may be added to the dry composition in the seed planter box.

In other embodiments, the contacting step may occur prior to adding the seeds to the seed planter box. For example, the seeds and dry composition may be mixed together and packaged prior to shipping to a planting site. Alternatively, the seeds may be mixed with the dry composition at the planting site prior to adding the seed/dry composition mixture to the seed planter box.

The seed planter may be a vacuum planter, a high-speed planter, an air planter, a plate planter, a plateless planter, a finger pickup planter, a row planter, a vegetable planter, or any other suitable planter. The dry composition may be added manually or mechanically (e.g., a mechanized metering system) to the seed planter.

Figure 2:
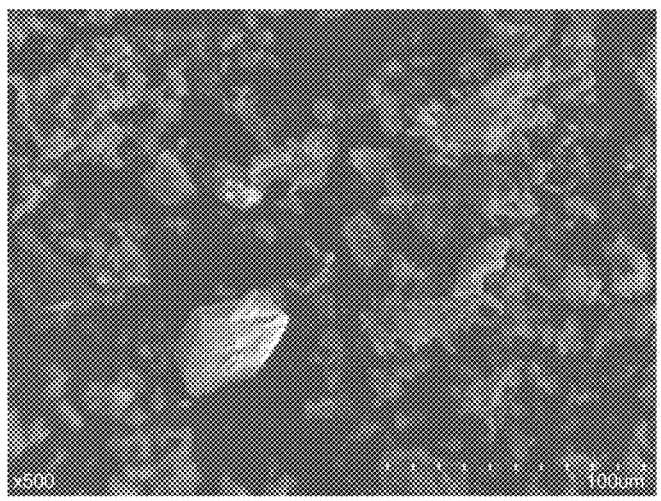
FIG. 2 shows a micrograph of talc seed lubricant.
Figure 3:
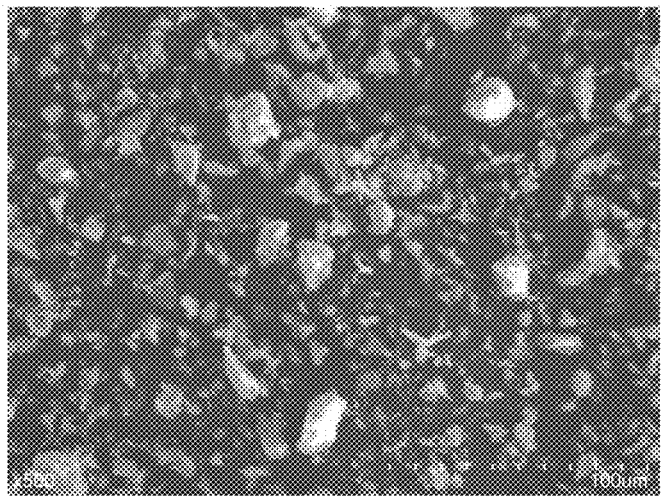
FIG. 3 presents a micrograph of graphite seed lubricant.
Figure 4:
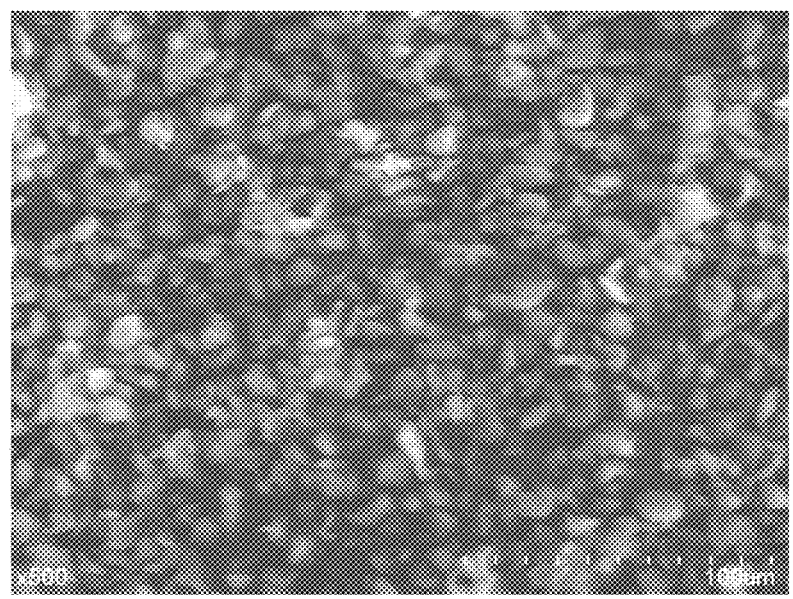
FIG. 4 present a micrograph of a polyethylene-based seed lubricant.

In general, the protein powder in the dry composition comprises particles having a spherical shape (see FIG. 1). Such particles reduce the coefficient of friction by reducing the area of contact. The spherical shape also introduces a rolling element which further lessens abrasion and formation of plant seed dust (i.e., naturally-occurring chaff or debris from the seeds and/or the coatings of treated seeds). Thus, the protein particles may act like ball bearings when they interact with the seeds in the planter box, thereby reducing friction, abrasion, and dust formation. In contrast, commonly-used seed lubricants comprise platy particles with irregular shapes and sizes (see FIGS. 2-4).

The amount of dry composition disclosed herein contacted with the seeds can and will vary depending upon the composition of the dry composition and the type of seeds. In general the weight ratio of the dry composition to the seeds may range from about 0.0001:1 to about 0.5:1. In certain embodiments, the weight ratio of the dry composition to the seed may range from about 0.005:1 to about 0.01:1. In other embodiments, about 50-300 grams, about 100-250 grams, or about 150-200 grams (i.e., about 4-8 ounces, or about 6 ounces) of the dry composition may be contacted with about 80,000 corn seeds or about 140,000 soybean seeds.

Contacting the seeds with the dry compositions disclosed herein improves seed flowability or seed lubricity in the seed planter and prevents seed clumping or bridging in the seed planter. Seed flowability (or dry flow rate) can be measured using a funnel flow test. In various embodiments, seed flowability may be increased by at least 5%, at least 10%, at least 15%, at least 20%, at least 25%, at least 30%, at least 35%, at least 40%, at least about 45%, at least about 50%, or more than 50% relative to seeds not contacted with the dry composition.

The dry compositions disclosed herein may also reduce wear on the planter or parts thereof, e.g., the plates of a planter.

Contact with the dry composition disclosed herein may also reduce seed dust formation by at least 0.1-fold, at least 0.5-fold, at least 1-fold, at least 2-fold, at least 3-fold, at least 4-fold, at least 5-fold, or more than 5-fold relative to seeds not contacted with the dry composition.

Contacting the seeds with the dry compositions disclosed herein may also increase the plantability of the seeds. Plantability refers to the number of seeds planted per planting opportunity. In various embodiments, seed plantability may be increased by at least 1%, at least 2%, at least 4%, at least 6%, at least 8%, at least 10%, at least 12%, at least 14%, or more than 14% relative to seeds not contacted with the dry composition.

Contact with the dry compositions disclosed herein may also increase emergence of the plant. Emergence refers to the number of viable plants per number of seeds planted. In certain embodiments, plant emergence may be increased by at least 1%), at least 2%, at least 4%, at least 6%, at least 8%, at least 10%, at least 12%, at least 14%, or more than 14% relative to seeds not contacted with the dry composition. Moreover, contact with the dry compositions disclosed herein may also improve plant emergence under drought conditions at the time of planting. For example, plant emergence may be increased at least 1%, at least 2%, at least 4%, at least 6%, at least 8%, at least 10%, at least 12%, or more than 13% relative to seeds not contacted with the dry composition under drought conditions at the time of planting.

Contacting the seeds with the dry compositions disclosed herein may also increase crop yield, or the number of bushels harvested per acre of a given crop. In some embodiments, crop yield may be increased by at least 1%, at least 2%, at least 4%, at least 6%, at least 8%, at least 10%, at least 12%, at least 14%, or more than 14% relative to seeds not contacted with the dry composition.

DEFINITIONS

To facilitate understanding of the invention, several terms are defined below.

The term "emergence" refers to the number of viable plants per number of seeds planted. While early plant vigor is considered part of emergence, it is a more subjective evaluation.

The term "plantability" refers to the number of seeds planted per planting opportunity. Plantability is generally measured as singulation percentage=[planting opportunities—(skips and multiples)/planting opportunities]×100. The ideal percentage for plantability is 100.

The term "seed dust," as used herein, refers the naturally occurring components of the seed such as chaff or outer hull or husk, as well as the fine particulate matter easily dislodged from treated seeds that contains components of the treatment or coating applied to the treated seeds.

The terms "seed flow" or "seed flowability" refer to the uniformity and lack of resistance to the flow of seed through a system such as a seed planter.

"Singulation" is a measurement taken from the planter as plant seeds pass through the planter under given conditions.

The term "treated seeds" refers to plant seeds that are treated or coated with at least one active ingredient.

The term "yield" means the number of harvested bushels per acre of a given crop.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the invention.

Example 1. Field Test—Emergence

Field tests were conducted to compare the performance of a soy-based (SB) dry composition comprising 80-94% isolated soy protein to the performance of a mixture of graphite/talc. The seeds and the lubricant product were poured into the planter box and mixed together. The soy based dry composition was used at rates of 1, 2, or 4 cups per planter box. Tables 1 and 2 present the details of planting and the performance properties for corn and soybeans, respectively.

TABLE 1

Field Test - Corn

| Brand | Hybrid | Product | Planting | Plant Rate (seeds/acre) | Emergence (plants/acre) |
|---|---|---|---|---|---|
| A | 1 | SB - 2 cups | normal | 34000 | 34000 |
| A | 1 | graphite/talc | normal | 34000 | 34000 |
| A | 1 | SB - 4 cups | normal | 34000 | 33500 |
| A | 1 | graphite/talc | normal | 34000 | 34000 |
| B | 1 | SB - 1 cup | normal/dry | 35000 | 34000 |
| B | 2 | SB - 1 cup | normal/wet | 35000 | 33000 |
| B | 3 | SB - 1 cup | normal/wet | 35000 | 34000 |
| B | 4 | SB - 1 cup | rained while planting | 35000 | 33000 |
| B | 5 | SB - 1 cup | rained while planting | 35000 | 33500 |

TABLE 2

Field Test - Soybean

| Brand | Hybrid | Product | Planting | Plant Rate (seeds/acre) | Emergence (plants/acre) |
|---|---|---|---|---|---|
| C | 1 | SB - 1 cup | planted/flooded | 150000 | 144000 |
| C | 1 | graphite/talc | planted/flooded | 150000 | 144000 |
| C | 2 | SB - 1 cup | rained while planting | 140000 | 132000 |
| C | 2 | graphite/talc | rained while planting | 140000 | 136000 |
| C | 3 | SB - 1 cup | normal | 140000 | 138000 |
| C | 3 | graphite/talc | normal | 140000 | 136000 |

Example 2. Field Test—Plantability

Figure 5:
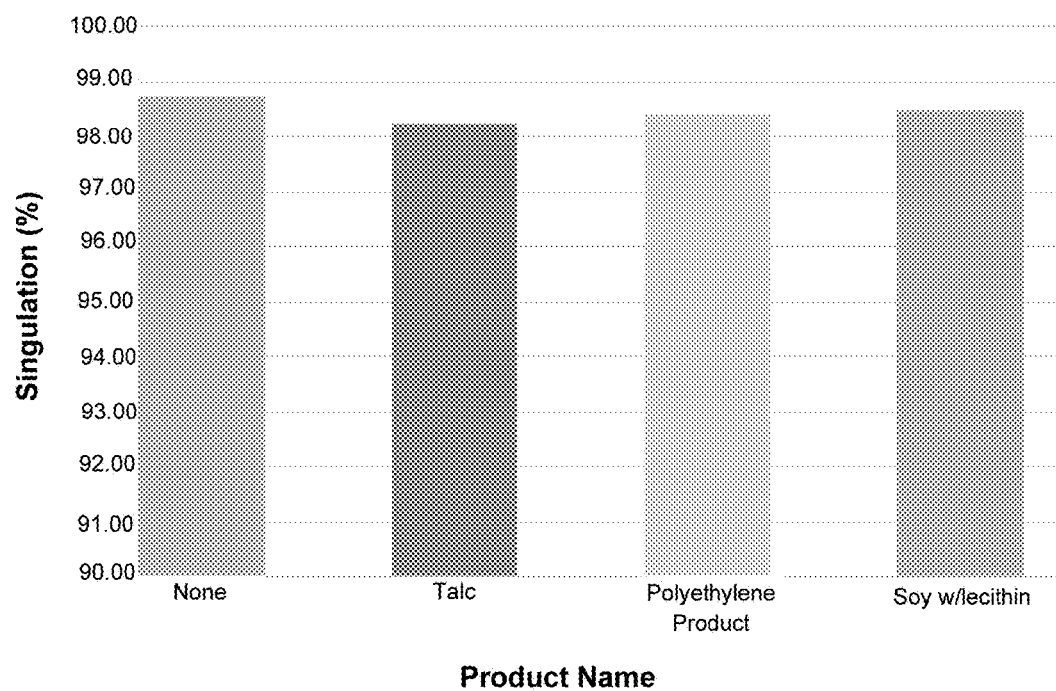
FIG. 5 presents a plot of the average percent singulation per indicated product for corn.
Figure 6:
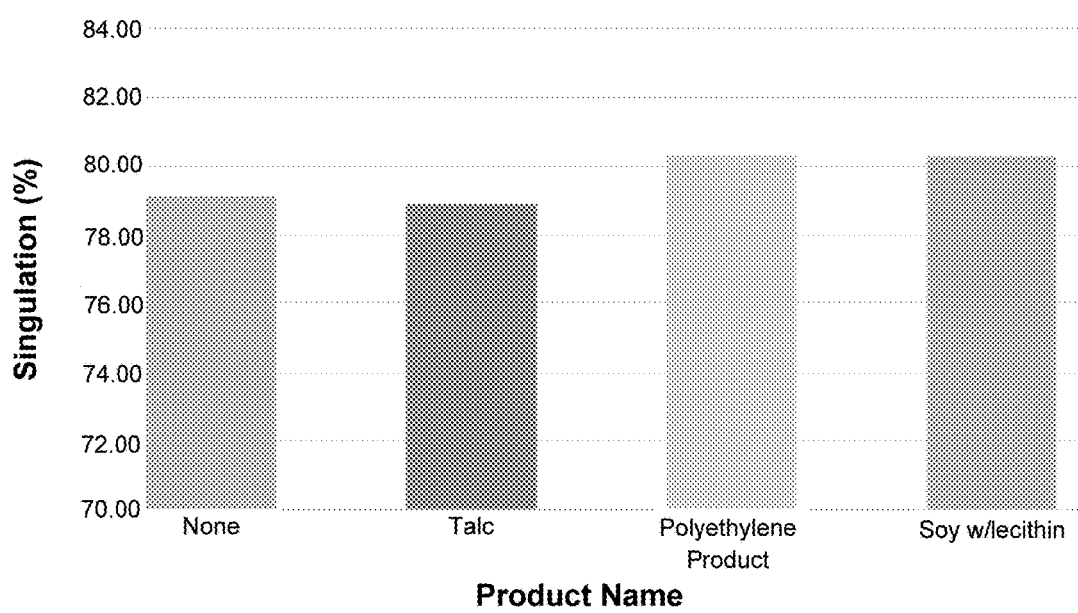
FIG. 6 shows a plot of the average percent singulation per indicated product for soybeans.

Field tests were conducted to compare the performance of a dry soy-based (SB) composition comprising isolated soy protein and soy lecithin to the performance of talc or a polyethylene-based (PE) lubricant. The seeds and the lubricant product were poured into the planter box (of a Horsch planter) and mixed together. Tables 3 and 4 present the plantability data, i.e., average % singulation, average % skips, and average % multiples for each product for corn and soybeans, respectively. The average percent singulation per product for corn and soybeans are presented in FIG. 5 and FIG. 6, respectively.

TABLE 3

Plantability Data - Corn

| Product | Brand | Size | Shape | Individual Average % Singulation | Indiv Ave % Skips | Indiv Ave % Multiples | Brand Ave % Singulation | Brand Ave % Skips | Brand Ave % Multiples | Product Ave % Singulation | Product Ave % Skips | Product Ave % Multiples |
|---|---|---|---|---|---|---|---|---|---|---|---|---|
| None | D | Sm | Flat | 98.10 | 1.30 | 0.60 | 98.83 | 0.63 | 0.53 | 98.75 | 0.82 | 0.43 |
| | | Med | Rnd | 99.00 | 0.40 | 0.60 | | | | | | |
| | | Lrg | Flat | 99.40 | 0.20 | 0.40 | | | | | | |

TABLE 3-continued

Plantability Data - Corn

| Product | Brand | Size | Shape | Individual Average % Singulation | Indiv Ave % Skips | Indiv Ave % Multiples | Brand Ave % Singulation | Brand Ave % Skips | Brand Ave % Multiples | Product Ave % Singulation | Product Ave % Skips | Product Ave % Multiples |
|---|---|---|---|---|---|---|---|---|---|---|---|---|
| | E | Sm | Rnd | 98.70 | 0.80 | 0.50 | 98.67 | 1.00 | 0.33 | | | |
| | | Med | Rnd | 98.10 | 1.70 | 0.20 | | | | | | |
| | | Lrg | Rnd | 99.20 | 0.50 | 0.30 | | | | | | |
| Talc | D | Sm | Flat | 98.30 | 0.90 | 0.80 | 98.87 | 0.47 | 0.67 | 98.23 | 1.20 | 0.57 |
| | | Med | Rnd | 99.00 | 0.40 | 0.60 | | | | | | |
| | | Lrg | Flat | 99.30 | 0.10 | 0.60 | | | | | | |
| | E | Sm | Rnd | 98.10 | 1.20 | 0.70 | 97.60 | 1.93 | 0.47 | | | |
| | | Med | Rnd | 96.60 | 3.20 | 0.20 | | | | | | |
| | | Lrg | Rnd | 98.10 | 1.40 | 0.50 | | | | | | |
| PE | D | Sm | Flat | 98.50 | 1.10 | 0.40 | 98.87 | 0.63 | 0.50 | 98.40 | 1.20 | 1.40 |
| | | Med | Rnd | 98.90 | 0.60 | 0.50 | | | | | | |
| | | Lrg | Flat | 99.20 | 0.20 | 0.60 | | | | | | |
| | E | Sm | Rnd | 98.30 | 1.40 | 0.30 | 97.93 | 1.77 | 0.30 | | | |
| | | Med | Rnd | 97.10 | 2.80 | 0.10 | | | | | | |
| | | Lrg | Rnd | 98.40 | 1.10 | 0.50 | | | | | | |
| SB | D | Sm | Flat | 97.10 | 2.00 | 0.60 | 98.47 | 0.97 | 0.57 | 98.47 | 1.05 | 0.48 |
| | | Med | Rnd | 98.70 | 0.70 | 0.60 | | | | | | |
| | | Lrg | Flat | 99.30 | 0.20 | 0.50 | | | | | | |
| | E | Sm | Rnd | 98.60 | 0.90 | 0.50 | 98.47 | 1.13 | 0.40 | | | |
| | | Med | Rnd | 97.70 | 2.00 | 0.30 | | | | | | |
| | | Lrg | Rnd | 99.10 | 0.50 | 0.40 | | | | | | |

TABLE 4

Plantability Data - Soybean

| Product | Brand | Size | Shape | Individual Average % Singulation | Indiv Ave % Skips | Indiv Ave % Multiples | Brand Ave % Singulation | Brand Ave % Skips | Brand Ave % Multiples | Product Ave % Singulation | Product Ave % Skips | Product Ave % Multiples |
|---|---|---|---|---|---|---|---|---|---|---|---|---|
| None | D | Lrg | Rnd | 75.40 | 10.60 | 14.00 | 79.17 | 9.33 | 11.53 | 79.11 | 9.09 | 11.82 |
| | | Med | Rnd | 79.20 | 9.40 | 11.40 | | | | | | |
| | | Med | Rnd | 82.90 | 8.00 | 9.20 | | | | | | |
| | | Lrg | Rnd | 78.80 | 9.10 | 12.10 | 79.06 | 8.84 | 12.10 | | | |
| | | Sm | Rnd | 77.13 | 10.63 | 12.24 | | | | | | |
| | | Sm | Rnd | 81.25 | 6.80 | 11.95 | | | | | | |
| Talc | D | Lrg | Rnd | 76.60 | 10.10 | 13.20 | 79.07 | 9.67 | 11.27 | 78.90 | 9.35 | 11.78 |
| | | Med | Rnd | 78.80 | 10.00 | 11.20 | | | | | | |
| | | Med | Rnd | 81.80 | 8.90 | 9.40 | | | | | | |
| | | Lrg | Rnd | 78.80 | 8.90 | 12.40 | 78.72 | 8.02 | 12.29 | | | |
| | | Sm | Rnd | 76.85 | 10.66 | 12.49 | | | | | | |
| | | Sm | Rnd | 80.52 | 7.51 | 11.97 | | | | | | |
| PE | D | Lrg | Rnd | 79.30 | 10.10 | 10.60 | 81.07 | 9.70 | 9.27 | 80.30 | 9.41 | 10.31 |
| | | Med | Rnd | 80.00 | 10.60 | 9.50 | | | | | | |
| | | Med | Rnd | 83.90 | 8.40 | 7.70 | | | | | | |
| | | Lrg | Rnd | 79.30 | 8.70 | 12.00 | 79.53 | 9.12 | 11.35 | | | |
| | | Sm | Rnd | 78.15 | 11.01 | 10.84 | | | | | | |
| | | Sm | Rnd | 81.15 | 7.65 | 11.20 | | | | | | |
| SB | D | Lrg | Rnd | 75.50 | 10.80 | 13.70 | 80.50 | 8.83 | 10.67 | 80.27 | 8.44 | 11.28 |
| | | Med | Rnd | 80.80 | 8.30 | 10.90 | | | | | | |
| | | Med | Rnd | 85.20 | 7.40 | 7.40 | | | | | | |
| | | Lrg | Rnd | 79.40 | 8.40 | 12.10 | 80.03 | 8.05 | 11.89 | | | |
| | | Sm | Rnd | 78.66 | 9.03 | 12.31 | | | | | | |
| | | Sm | Rnd | 82.03 | 6.71 | 11.25 | | | | | | |

What is claimed is:

1. A method for improving plant seed flowability and/or reducing formation of plant seed dust, the method comprising contacting a plurality of plant seeds with a dry composition comprising a protein powder and a lipid.

2. The method of claim 1, wherein the protein powder is a soy protein powder, a corn protein powder, an oat protein powder, a wheat protein powder, a pea protein powder, a rice protein powder, a nut protein powder, an algal protein powder, a kelp protein powder, a whey protein powder, a casein protein powder, an egg protein powder, an albumen protein powder, a blood meal protein powder, a bone meal protein powder, a fish protein powder, a shellfish protein powder, a plankton protein powder, a yeast protein powder, a bacterial protein powder, or a combination thereof.

3. The method of claim 1, wherein the lipid is a lecithin, a vegetable oil, a fish oil, an animal fat, or a combination thereof.

4. The method of claim 1, wherein the dry composition comprises an isolated soy protein powder and a soy lecithin.

5. The method of claim 4, wherein the isolated soy protein powder is present in an amount from about 80% to about 99.9% of the by weight of the dry composition and the soy lecithin is present in an amount from about 0.01% to about 5% of by weight of the dry composition.

6. The method of claim 1, wherein the dry composition further comprises an active ingredient chosen from a micronutrient, *rhizobium* inoculum, fertilizer, insecticide, fungicide, herbicide, or combination thereof.

7. The method of claim 1, wherein the contacting occurs in a seed planter box.

8. The method of claim 1, wherein the contacting occurs prior to adding the plurality of plant seeds to a seed planter box.

9. The method of claim 1, where the dry composition is contacted with the plurality of plant seeds in a weight ratio from about 0.0001:1 to about 0.5:1.

10. The method of claim 1, wherein the plurality of plant seeds is chosen from corn seeds, legume plant seeds, cereal seeds, grass seeds, cotton seeds, oil seeds, or vegetable seeds.

11. The method of claim 1, wherein the plurality of plant seeds contacted with the dry composition has increased seed plantability, increased plant emergence, and/or increased crop yield relative to plant seeds not contacted with the dry composition.

12. A dry composition for use as a seed flow lubricant, the dry composition comprising an isolated soy protein powder and a soy lecithin, wherein the isolated soy protein powder is present in an amount from about 80% to about 99.9% by weight of the dry composition and the soy lecithin is present in an amount from about 0.01% to about 5% by weight of the dry composition.

13. The dry composition of claim 12, wherein the dry composition further comprises an active ingredient chosen from a micronutrient, *rhizobium* inoculum, fertilizer, insecticide, fungicide, herbicide, or combination thereof.

14. A seed composition comprising a plurality of plant seeds and a dry composition, the dry composition comprising a protein powder and a lipid.

15. The seed composition of claim 14 wherein the protein powder is a soy protein powder, a corn protein powder, an oat protein powder, a wheat protein powder, a pea protein powder, a rice protein powder, a nut protein powder, an algal protein powder, a kelp protein powder, a whey protein powder, a casein protein powder, an egg protein powder, an albumen protein powder, a blood meal protein powder, a bone meal protein powder, a fish protein powder, a shellfish protein powder, a plankton protein powder, a yeast protein powder, a bacterial protein powder, or a combination thereof, and the protein powder is present in an amount from about 50% to about 99.9% by weight of the dry composition.

16. The seed composition of claim 14, wherein the lipid is a lecithin, a vegetable oil, a fish oil, an animal fat, or a combination thereof, and the lipid is present in an amount from about 0.005% to about 0.5% by weight of the dry composition.

17. The seed composition of claim 14, wherein the dry composition further comprises an active ingredient chosen from a micronutrient, *rhizobium* inoculum, fertilizer, insecticide, fungicide, herbicide, or combination thereof.

18. The seed composition of claim 14, wherein the dry composition comprises an isolated soy protein powder and a soy lecithin.

19. The seed composition of claim 18, wherein the isolated soy protein powder is present in an amount from about 80% to about 99.9% by weight of the dry composition and the soy lecithin is present in an amount from about 0.01% to about 0.5% by weight of the dry composition.

20. The seed composition of claim 19, wherein the dry composition further comprises an active ingredient chosen from a micronutrient, *rhizobium* inoculum, fertilizer, insecticide, fungicide, herbicide, or combination thereof.

21. The seed composition of claim 14, wherein the plurality of plant seeds is chosen from corn seeds, legume plant seeds, cereal seeds, grass seeds, cotton seeds, oil seeds, or vegetable seeds.

* * * * *